United States Patent [19]

Marks

[11] Patent Number: 4,819,653
[45] Date of Patent: Apr. 11, 1989

[54] MULTI-FUNCTION FLUID COMMUNICATION CONTROL SYSTEM

[75] Inventor: Lloyd A. Marks, 29 Woody Ln., Northport, N.Y. 11768

[73] Assignee: Lloyd A. Marks, Bryn Mawr, Pa.

[21] Appl. No.: 850,758

[22] Filed: Apr. 11, 1986

[51] Int. Cl.⁴ .............................................. A61B 5/02
[52] U.S. Cl. .................................. 128/673; 128/748; 251/129.03
[58] Field of Search ........................... 128/672–673, 128/674, 675, 748; 251/129.01, 129.03, 129.04; 137/625, 625.17, 614.05–614.06

[56] References Cited

U.S. PATENT DOCUMENTS

| | | |
|---|---|---|
| 2,564,977 | 8/1951 | Hsi Hu . |
| 3,143,111 | 8/1964 | Green . |
| 3,157,201 | 11/1964 | Littmann . |
| 3,665,955 | 5/1972 | Conner, Sr. ............... 251/129.04 X |
| 3,741,248 | 6/1973 | Stevens, Jr. ............... 251/129.04 X |
| 3,893,452 | 7/1975 | Birnbaum . |
| 3,938,506 | 2/1976 | Birnbaum et al. . |
| 4,080,966 | 3/1978 | McNally et al. . |
| 4,112,272 | 9/1978 | Jonsson et al. ................. 200/61.58 |
| 4,143,851 | 3/1979 | Lange ........................... 60/416 X |
| 4,285,496 | 8/1981 | Coles ............................ 251/129.03 |
| 4,299,251 | 11/1981 | Dugas ........................... 128/675 X |
| 4,431,009 | 2/1984 | Marino, Jr. et al. ............ 128/675 |
| 4,464,172 | 8/1984 | Lichtenstein .................... 604/65 |
| 4,508,103 | 4/1985 | Calisi .............................. 128/673 |
| 4,562,845 | 1/1986 | Furst et al. ....................... 128/675 |
| 4,566,480 | 1/1986 | Parham ............................ 604/32 X |
| 4,608,996 | 9/1986 | Brown ........................... 128/748 X |

FOREIGN PATENT DOCUMENTS

| | | | |
|---|---|---|---|
| 3207044 | 10/1983 | Fed. Rep. of Germany ...... 128/673 |
| 0040302 | 3/1980 | Japan ............................ 251/129.04 |

Primary Examiner—Kyle L. Howell
Assistant Examiner—Angela D. Sykes
Attorney, Agent, or Firm—Hoffmann & Baron

[57] ABSTRACT

The present invention is a multi-function fluid communication control system for effecting selective automated control to provide selected fluid communication between fluid reservoirs, instruments, and various pressure conditions which can be used in, for example, a catheterization procedure. The system includes multiport fluid communication valves, such as three-port stopcocks which are connected as required by fluid conduits such as tubes. Each of the valves, in turn, are connected to a control mechanism such as stepper motors to provide the necessary fluid communication paths in response to the user's requirements. User requirements can be translated into the required valve movements through command signals operated by, for example, an appropriately programmed computer or microprocessor.

21 Claims, 4 Drawing Sheets

MULTI-FUNCTION FLUID COMMUNICATION CONTROL SYSTEM

BACKGROUND OF THE INVENTION

The present invention relates to the art of controlling fluid communication between and among various fluid parts to effect hydraulic communication between fluid reservoirs, sources, instruments, as well as various pressure conditions.

It has been known in the art of multiple hydraulic connections to provide series of multiple port valves in order to effect desired fluid communication paths for many purposes. For example, since it is generally required to provide various fluid communication paths in order to measure pressure, calibrate equipment and clean and purge hydraulic systems, multi-port valves can be used which combine fluid connection and blockage of multiple hydraulic communication ports. In the case of medical applications, hydraulic connections can be particularly critical especially since hydraulic lines can be in direct communication with human fluid conduits such as vessels, arteries, etc. Thus, a failure of a hydraulic system could result in severe damage to the patient.

Furthermore, in the art of medical care it has been known to provide a computer controlled medical care system in which automatic or manual control of a variety of medical procedures inlcuding diagnostic procedures can be carried out. Thus, in U.S. Pat. No. 4,464,172 to Lichtenstein, it is known to perform a number of procedures such as infusion of physiologic fluids, monitoring of hemodialysis, ultrafiltration, hemofiltration, medical drainage and irrigation procedures, etc. This system is designed basically to monitor, by use of sensors, the flow to or from the body and to generate command signals necessary to either stop, start, or otherwise modify the flow into or out of the body and/or effect analysis of such fluid.

In U.S. Pat. No. 4,112,272 to Jonsson, et al. a measuring device is disclosed which transmits signals to a device having an electro-mechanical switch and valve mechanism for switching off to automatic zero balance and automatically calibrate. This disclosure shows the manipulation of an instrument responsive to flow in and out of a body wherein a signal is generated to a control unit.

While these devices, as well as others, may prove adequate with regard to flow directly into and out of a body, they are inadequate for operation of a multifunction fluid communication system which requires simultaneous and/or step-wise control of multi-port control valves connecting various fluid sources, reservoirs, instruments, and fluid-effecting environments.

There has been, however, a need for a multifunction fluid communication control system in the medical field, especially in an area of catheterization processes and systems. In a cardiac catheterization procedure, a flexible plastic tube is positioned in the heart to perform various diagnostic tests, and several fluid communication paths must be continuously established in order to perform the many tasks associated with making a proper diagnosis. For example, not only do the doctor and attending technicians have to be able to continuously monitor pressure within the cardiac chambers, but the system must continuously or periodically be flushed to remove blockages and clotting, as well as periodic calibration be performed on the pressure measuring instrumentation in order to achieve accurate readings.

Other procedures not associated with catheterization also require a multi-function fluid communication control system to combine operations such as infusion, flushing, pressure measurement, dye injection, blood extraction, etc. which require simultaneous and step-wise control of various fluid and pressure conditions.

Thus, it is an object of the present invention to provide a control system which provides multiple fluid communication paths between various fluid sources, reservoirs, instrumentation, and pressure conditions.

Another object of the present invention is to provide a system whereby such fluid communication paths can be provided quickly and efficiently in a simultaneous or step-wise fashion.

Yet another object of the present invention is to provide such a system which gives not only the operating doctor, but also various technicians and assistants control over such system.

Still another object of the present invention is to provide a system of the type described above which can be readily adapted to a medical environment and used in combination with existing surgical equipment and arrangements.

Other and further objects will become apparent to those skilled in the art upon review of the following technical disclosure.

SUMMARY OF THE INVENTION

The present invention is a multi-function, fluid communication control system for simultaneous and step-wise connection of fluid communication between ports of hydraulically connected multi-port fluid communication valves.

The present system, which is especially effective for use in a catheterization process, includes a command means for sending command signals to a function control, such as a computer control means. The command means can be any kind of control mechanism, including a control panel or one or more remote control mechanisms, which send electrical command signals to the function control.

The function control means, as indicated above, can be a computer control means which translates the command signals to multiple valve instruction signals which are then transmitted to control means for manipulating the multi-port fluid communication valves.

Finally, the control means can include electrically-driven motors attached to the multi-port fluid communication valves for mechanical manipulation thereof responsive to the instruction signals.

As a result of the present invention, an accurate and efficient system is provided for quickly configuring the different mutiple port hydraulic communication valves to make the necessary connections to perform many of the tasks required in the multifunction system.

Moreover, additional functions can be added and all functions automated to periodically occur without the attention of an operator.

In the case of use of such a system in a catheterization process, the otherwise tedious and repetitive tasks of taking pressure measurements, flushing, calibrating, and purging the system of air bubbles, can be very simply effected and controlled even at remote positions by the operating doctor and/or technicians and assistants without the necessity of having to traverse a crowded medical environment and manually making the adjustments of all of the different multi-port control valves.

Furthermore, in the case of a cardiac catheterization process, the present system provides a means for continual pressure measurement with periodic flush cycles which keep the fluid communication lines clear of clotting, such function being performed markedly better and sometimes by necessity under a pressurized flush than with a drip flush.

Additionally, the present invention can also be provided with air bubble detection means to prevent introduction of bubbles into the catheterization process, and optico-electrical detection devices can be easily employed to insure accurate positioning of the multi-port fluid communication valves in each of the required configurations. Other feedback detection devices can be employed as required.

For a better understanding of the present invention, together with other and further objects, reference is made to the following description, taken in conjunction with accompanying drawings and its scope will be pointed out in the appended claims.

BRIEF DESCRIPTION OF THE DRAWINGS

A preferred embodiment of the invention has been chosen for purposes of illustration and description and is shown in the accompanying drawings wherein:

FIG. 6a is a view of the mechanical linkage in FIG. 6 taken from lines 6a—6a;

DETAILED DESCRIPTION OF THE INVENTION

Referring to the FIGS., there can be seen a multifunction, fluid communication control system which can be used to make simultaneous or step-wise hydraulic connections between various sources and reservoirs of fluid as well as different instrumentation and pressure conditions. In particular, the system shown in the FIGS. depicts one which is particularly useful in a cardiac catheterization process.

A cardiac catheterization process provides a means to probe the heart region and detect any diseases or malfunctions. One of the major problems in the procedure is the ineffeciency which occurs when technicians have to take time to turn the various multi-port valves or stopcocks in order to achieve the different process conditions.

Figure 1:
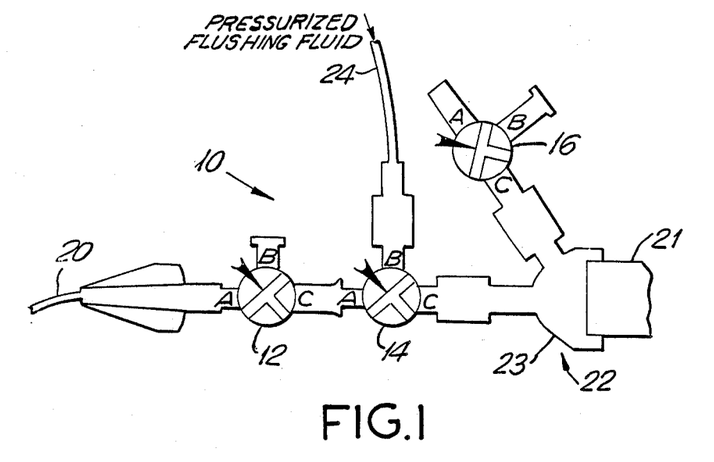
FIG. 1 is a schematic of a system in accordance with the present invention which can be used in a cardiac catheterization process.

As a part of the process, a catheter, which is a thin, flexible plastic tube, is passed through a blood vessel and into the heart for measuring pressures, taking blood specimens, and administering medications or radiopaque dyes for cineangiography (high speed motion X-rays). In order to perform these tasks, connections must be made in varying combinations between the cardiac catheter, a pressure transducer, a pressurized flush solution, and ambient atmosphere. In FIG. 1 a schematic is shown of the system 10 which is used in such a process. In particular, there are shown three stopcocks, 12, 14 and 16, each one of which has three fluid communication ports A, B and C.

Figure 1A:
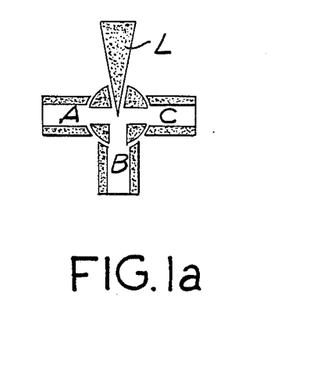
FIG. 1a is a schematic of a three-way stopcock which can be used in the present invention.

With particular reference to FIG. 1a, it can be seen that the stopcocks which are useful in the system shown herein have an internal rotating T-shaped channel which establishes connections for fluid communication among the three ports. (Please refer to FIG. 6 for a perspective view of a typical stopcock used in a catheterization procedure). The stopcocks are arranged so that when the lever L points towards one of the three channels, that channel is disconnected from the other two, the other two having fluid communication established therebetween. Thus, when the lever is pointed toward the B port, the B port is closed to fluid communication, while ports A and C are hydraulically connected. Similarly, when the stopcock lever L is pointed toward the A port, that port is blocked from fluid communication while ports B and C are hydraulically connected; and when the lever L is pointed toward the C port, it is blocked from fluid communication, while ports A and B are hydraulically connected.

In the schematic shown in FIG. 1, a catheter tube 20, which can be passed through a blood vessel and into the heart in a catheterization process, is connected for fluid communication to port A of stopcock 12. Port B of stopcock 12 is connected to ambient atmosphere and Port C is connected to stopcock 14. Meanwhile, stopcock 14 is connected by its port A to stopcock 12, by port C to a pressure measurement means 22, and by its port B to a source of pressurized flushing fluid.

The pressure measurement means 22 can include a pressure transducer 21 and a pressure measurement dome 23. The pressure transducer dome 23 is usually a clear plastic structure which contains fluid and is used for connection to the catheter. If a dome is used, it must be opened to ambient atmosphere (or room air) in order to calibrate the transducer and recorder.

Stopcock 14 is connected for hydraulic communication with a source of pressurized flushing fluid by line 24, which, in the case of a cardiac catheterization process, can be heparinized saline solution under about 150 mm Hg.

A third stopcock 16 is connected for fluid communication by its outlet port C to the pressure measurement means 22 through dome 23, while ports A and B are opened to the ambient atmosphere.

The principle tasks which require manipulation of the stopcocks during a procedure such as a cardiac catheterization include, in addition to the normal pressure measurement operation, flushing of the catheters, flushing of the pressure dome, and recording of pressure tracings. Since any number of catheters may be used depending on the nature and the purpose of the cardiac catheterizatoin, e.g., in a typical right and left study, two catheters are used, one positioned in an artery and the other in a vein, it is necessary to flush all the catheters every few minutes with a heparinized saline solution to prevent clots from forming. Thus, it can be seen that in order to keep the catheter lines open, a great deal of manipulation is required. Catheters are also flushed every time specimens are withdrawn from them, prior to pressure recordings, and whenever pressure wave forms become damped.

Figure 2:
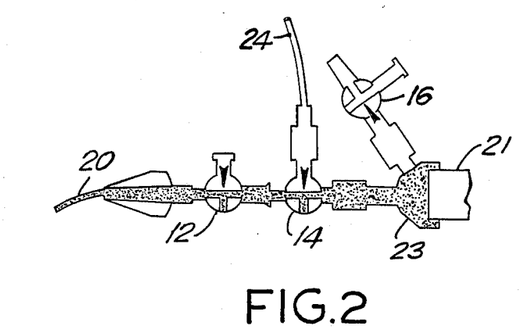
FIGS. 2-5 are schematic which show the different settings required for effecting the different modes of operation, in, for example, a catheterization process.

Most of the time during the procedure, the elements of a cardiac catheterization system are connected for pressure measurement. As shown in FIG. 2, the stopcocks are positioned to hydraulically connect the catheter directly to the transducer dome 23, (the dark portion represents fluid communication and the arrow shows the position of the stopcock lever). When the system is connected to an automatic function control system, the stopcocks can be left in this position as a default condition.

Figure 3:
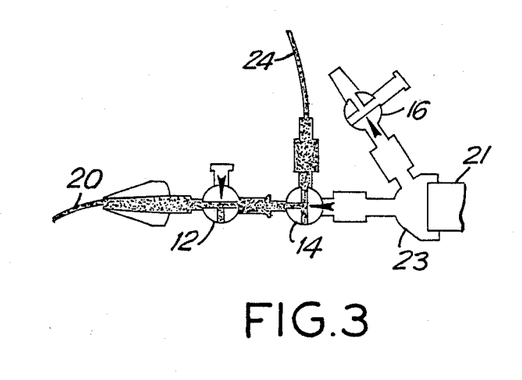

In FIG. 3, the next mode of operation depicted is a flushing mode, by which the pressurized flushing solution is connected to the catheter. After a flush is completed, the stopcocks can be repositioned to measure pressure. In FIG. 3 the dark portion shows a fluid communication between the source of pressurized flush fluid through line 24, stopcocks 14 and 12, and thence into the catheter 20.

Figure 4:
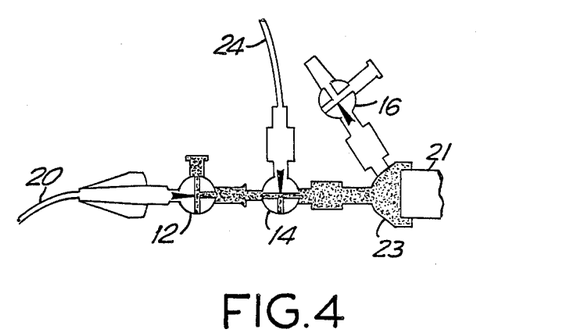

FIG. 4 shows a configuration used to establish a zero base line with regard to the ambient atmosphere in order to make an accurate recording or tracing of the cardiac pressure. In particular, FIG. 4 shows fluid communication between the ambient air through stopcock 12 and stopcock 14 and thence to the pressure measurement device 22. After the recorder base line has been calibrated to zero with the stopcocks in this condition, the catheter can be flushed as shown in FIG. 3 and the stopcocks returned to the pressure measurement mode of FIG. 1 so that the pressure can be measured and recorded.

Figure 5:
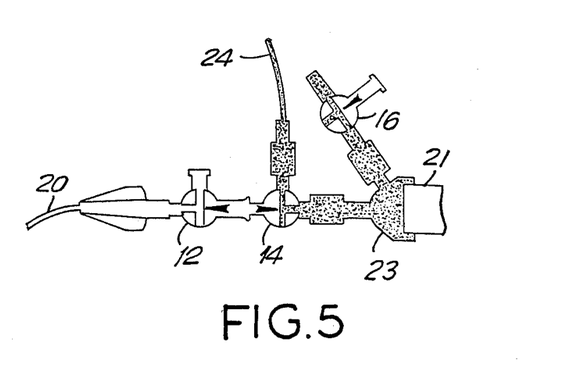

Yet a further operation which must be performed in order to make the system effective for purposes of cardiac catheterization is to purge the system of air bubbles which may accumulate in the pressure dome 23 so that pressure readings will not be damped. Consequently, the dome should be flushed clear at least at the beginning of each procedure to purge the air bubbles accumulated therein. In FIG. 5, the stopcocks are shown to establish a fluid communication directly between the source of pressurized flush fluid, the pressure dome, and thence the ambient atmosphere through stopcock 16 for forcing out air bubbles which may be accumulated therein. Inasmuch as bubbles may adhere to the surface of the pressure measurement device and/or the interior surface of the pressure dome, agitation may be needed to jolt the bubbles free from their lodged condition.

In summary Table 1 shows the correlative positions of each of the stopcock levers for the functions described above.

TABLE 1

| Function | Stopcock #12 | Stopcock #14 | Stopcock #16 |
|---|---|---|---|
| Pressure Measurement | B | B | C |
| Flushing Catheter | B | C | C |
| Transducer Calibration | A | B | C |
| Purging Transducer Dome | B | A | A or B |

Needless to say, manipulating the stopcocks in the catheterization lab is tedious, repetitive and time consuming. The pressure transducer and stopcocks are usually located at some distance apart, so that every time a catheter or pressure dome is flushed, a technician must interrupt their ongoing tasks and walk to and from the stopcocks in order to make the necessary changes in the hydraulic connections. Furthermore, when a pressure recording is made, it is necessary to make at least two trips in order to open the transducer to ambient atmosphere for calibration of the recorder, followed by calibrating the recorder and back again to flush the lines and set them for pressure measurement. In order to eliminate in whole or in part these unnecessary steps, the technician and/or doctor can be provided with a control, even multiple remote controls at more than one station, so that stopcock manipulation can be achieved therefrom without physical movement.

Figure 6:
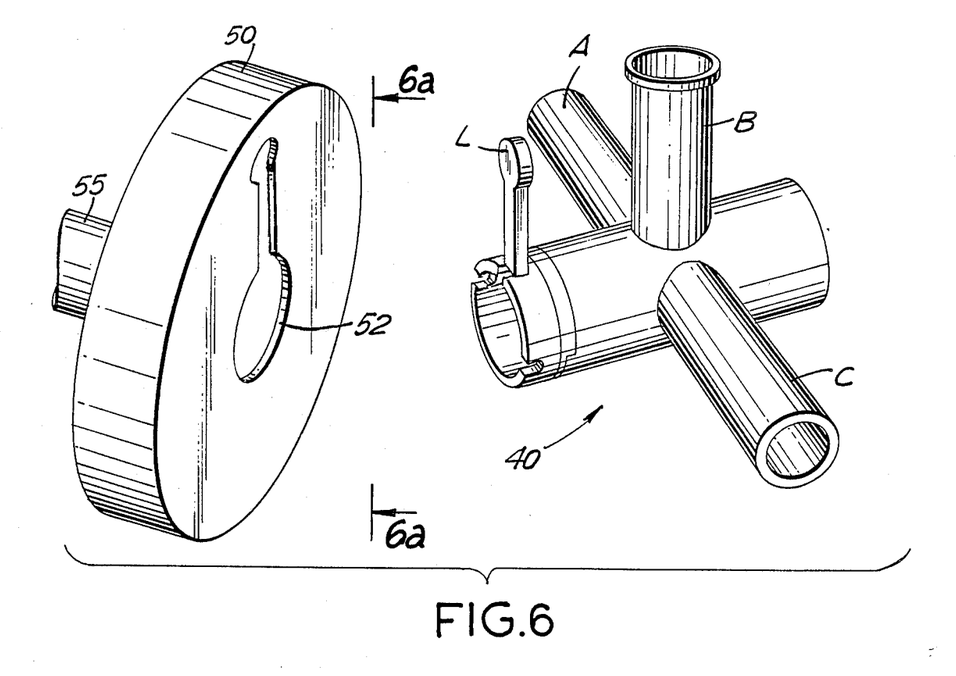
FIG. 6 is an exploded perspective view of a typical stopcock used in the process shown in FIGS. 1-5 and a mechanical linkage which can be attached thereto.

In order to make this process more efficient, it has been found that a mechanical linkage such as that shown on the left hand side of FIG. 6 can be provided for stopcocks known in the art, which will turn them in response to an instruction signal generated by an appropriate control unit 60. Thus, the system can take user input via even remote control switches and effect mechanical turning of the stopcocks simultaneously or step-wise thus saving time and allowing operators to accomplish more by doing other required procedural tasks.

In particular, there is shown in FIG. 6 a stopcock 40 having ports A, B and C and a lever L which can fit into a disk 50 mounted on a drive 55. The disk 50, in turn, contains a template depression 52 in the form of lever L and slightly larger than lever L so that the lever can be inserted into the depression for being driven simultaneously therewith. The drive shaft 55 in turn can be connected to stepper motors 70 which can be rotated in precise increments in a clockwise or counterclockwise direction. While the invention is not intended to be so limited, it has been found that this is a particularly useful mechanical linkage for the present process since it can be made to be compatible with known equipment techniques.

Figure 6A:
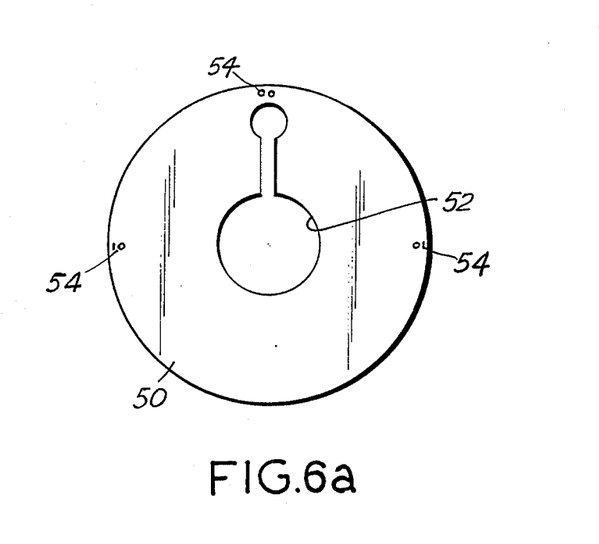

Moreover, the stopcock positions can be easily verified with an optical electronic feedback system by detection of reflective tape 54 shown in FIG. 6a, each position of which can be identified by a two digit binary code. Basically, light reflects from the tape and switches a pair of phototransistors, providing a two-bit digital feedback signal for each stepper motor. Alternatively, other known feedback systems can be employed.

In order to provide the function control to the stepper motor, the system can be provided with a computer control means 60 to send the appropriate electrical signals to each of the stepper motors to effect the different operations. The computer control system can be a combination of a central processing unit and software and drive circuitry, or, in the alternative, can include a microprocessor having appropriately programmed microchips which can effect the different conditions.

Figure 7:
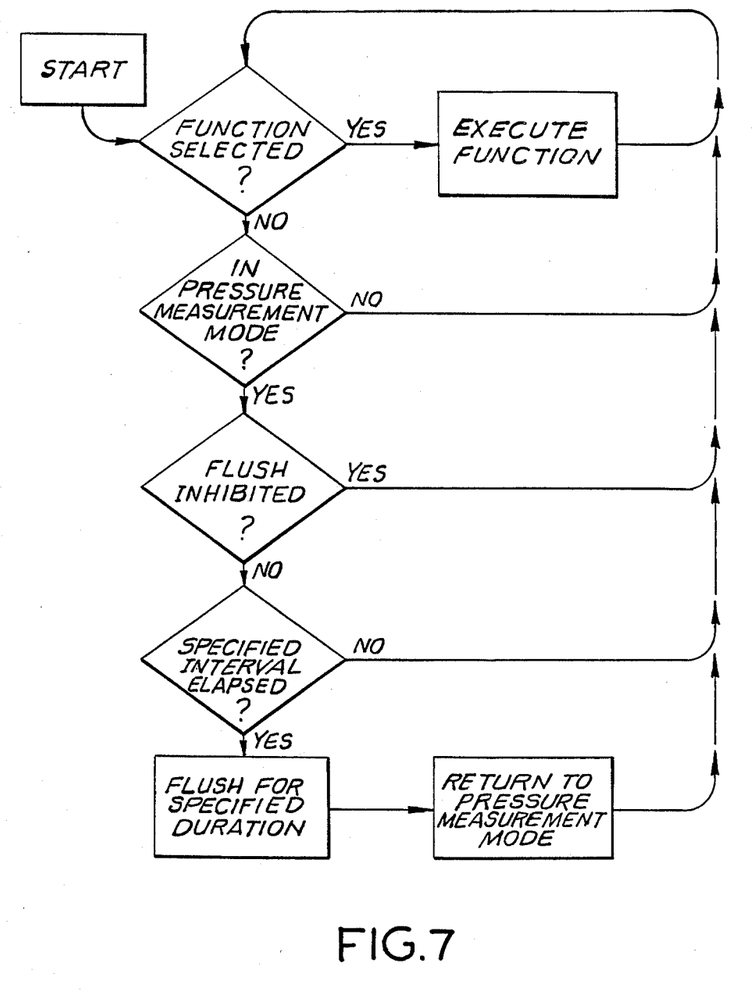
FIG. 7 is an operational flow diagram useful in a computer control means which can be used in the present invention.
Figure 8:
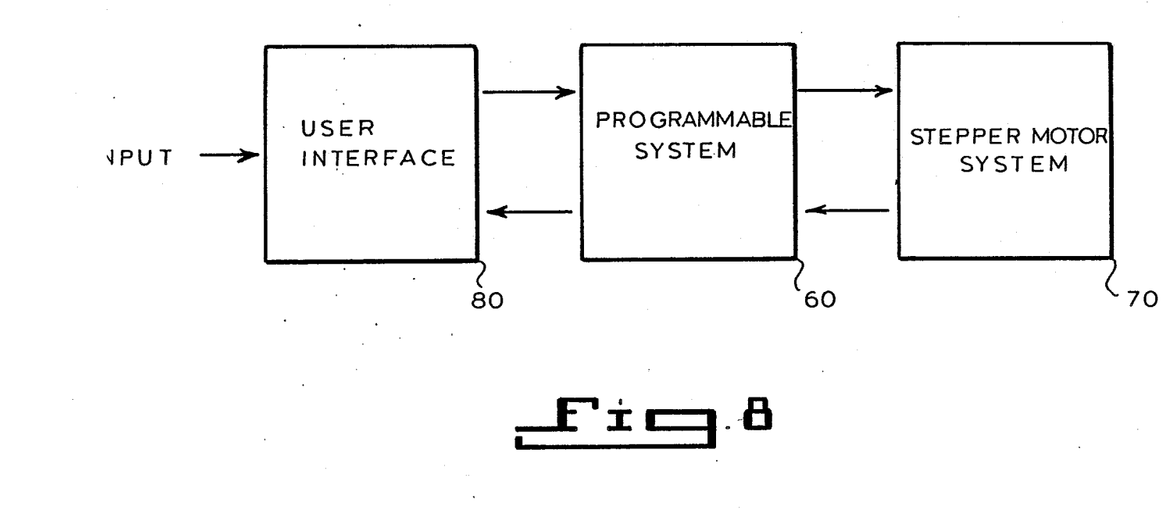
FIG. 8 is a diagrammatical representation of the control system of the present invention.

Referring to FIG. 7, a general flow diagram is shown which depicts an effective mode of operation for a computer control used in the present invention. Basically, the computer control continuously interrogates the input 80 from the user to determine if a function has been selected which is outside of the routine operation of the control system. If no function has been selected by the operator by means of a switch or button or otherwise, the system will operate in a pressure measurement mode and, in the absence of a flush inhibit command, will direct a flush of the catheter lines at specified intervals, e.g., for about 3 seconds every one minute. Once the flush cycle has been completed, the computer will automatically return to the pressure measurement mode and continue to interrogate the system for a selected function input. Thus, it can be said that the stopcocks are maintained by the computer in a pressure measurement condition as a default condition and will execute flushing at specified intervals and for specific durations throughout the default condition. The pressure measurement condition is shown in FIG. 2 and the flush condition is shown in FIG. 3.

One of the functions which can be selected is flushing of the pressure dome in order to purge the system of air bubbles. The hydraulic connection for this operation is shown in FIG. 5, and is usually performed at least before each procedure in order to eliminate air bubbles in the system. In one embodiment, stopcock 16 will not be connected to the automated system, but rather will be manipulated by hand in order to allow the operator to impart agitation of the pressure measurement device to jolt the bubbles free from their normally lodges condition. Once this operation has been completed, the operator can then return the system to a pressure measurement mode shown in FIG. 2.

When a pressure recording is to be taken, the operator will first calibrate the recording instruments by making a zero calibration with respect to the ambient atmosphere. The hydraulic communication path for this is shown in FIG. 4 and will be effected by merely actuating the appropriate control to the computer control means and zeroing the recording device while the pressure measuring means is exposed to the ambient pressure. Once this is completed, the system will be flushed with pressurized flushing fluid as shown in FIG. 3 and then connected for pressure measurement as shown in FIG. 2. Since it is not desired to have a periodic flushing during pressurement recording operation, a flush inhibit command will be sent to the computer control means to eliminate the periodic flushing operation which usually occurs in the pressure measurement mode.

In order to determine the effectiveness of the present system, experiments were conducted using two subjects who performed each of the principle tasks indicated herein ten times, both with the traditional manual method, and by use of the present automated system. These experiments were conducted under simulated catheterization laboratory environment conditions wherein the control panel was positioned four steps from the stopcocks and pressure transducer. Since two catheters are normally used, the time to execute two sequential flushes was considered the time of a routine flush.

It is noted that the present control system requires no operator time whatsoever to execute a routine flush. Since, it was found that the time required to perform sequential flushed on two catheters is about 15.1 seconds, thus the savings by use of the present system is the entire time of approximately 15 seconds.

In another comparison, it has been found that the difference in the time required to execute a single manual flush as compared to an automatically commanded flush of the present system is almost 9 seconds per flush.

Perhaps even more dramatically, it has been found that the difference in the time required to manipulate the stopcocks to make a pressure measurement as compared to making such a pressure recording by use of this system, is 15½ seconds per recording.

Inasmuch as a typical, uncomplicated, complete right and left heart study, there are approximately 20 routine flushes, 8 intermittent flushes, 16 pressure recordings and two dome flushes, it has been calculated that the total potential time savings was greater than 10 minutes for both of the subjects of the experiment. This can easily equal or exceed 15 to 20 percent of the total time required to complete a case after vessel access has been achieved. Thus, the efficiency of the present invention can be dramatic in known catheterization and related processes which require multi-function fluid communication control of multiple hydraulic connections.

Accordingly, while there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

I claim:

1. Multi-function fluid communication control system for effecting selective automated simultaneous and step-wise connection for fluid communication between fluid reservoirs, fluid sources, instruments, and various pressure conditions, comprising
    more than one stopcock multi-port fluid communication valve, each said stopcock having fluid path selection levers,
    fluid passage conduits connecting ports of each of said stopcocks to provide said selective fluid communication between said fluid reservoirs, sources, instruments, and various pressure conditions responsive to command signals, said control means comprising stepper motors connected for selective step-wise adjustment of said stopcocks to provide desired fluid flow between certain ports and a programmable electrical signal-sending unit for sending electrical signals to said stepper motor, said stepper motors connected to said stopcocks by means of a linkage from an output drive armature of said motor to a means for directly driving said levers whereby said stopcocks are selectively adjusted, and
    command means connected to said control means for delivery of command signals thereto whereby said selective fluid communication connections are effected.

2. The system of claim 1 wherein said means for directly driving said levers is a direct drive template disk into which said levers fit whereby said stopcocks are selectively adjusted.

3. The system of claim 1 wherein said command means comprises a user interface for receipt of function selection from a user.

4. The system of claim 1 wherein said programmable electrical signal-sending unit is a central processing unit with drive circuitry to provide electric signals to selectively adjust said stepper motors, and appropriate software to automatically adjust said stepper motors responsive to user input and in the absence of user input.

5. The system of claim 1 wherein said programmable electrical signal-sending unit is a microprocessor with microchips which provide electric signals to selectively adjust said control means.

6. The system of claim 1 which is a catheterization system wherein said multi-port fluid communication valve comprises three stopcocks, a first stopcock arranged for fluid communication between any two of the atmosphere, a catheter tube leading to the body, and a second three-port stopcock, said second stopcock arranged for fluid communication between any two of said first stopcock, a pressure measurement chamber, and a source of pressurized flushing fluid, and a third stopcock arranged to provide in fluid communication with said pressure measurement chamber and the atmosphere, whereby said system can be selectively adjusted to perform pressure measurement, catheter flushing, calibration and air purging.

7. The system of claim 6 wherein said first stopcock is arranged for fluid communication between only said catheter and said second stopcock, said second stopcock is arranged for fluid communication between only said first stopcock and said pressure measurement chamber, and said third stopcock is arranged to block fluid communication between said pressure chamber and said ambient atmosphere whereby said vascular pressure measurement is taken.

8. The system of claim 6 wherein said first stopcock is arranged for fluid communication between only said catheter and said second stopcock, said second stopcock is arranged for fluid communication between only said source of pressurized fluid and said pressure chamber whereby flushing of said catheter tube is effected.

9. The system of claim 6 wherein said first stopcock is arranged for fluid communication between only the ambient atmosphere and said second stopcock, and said second stopcock is arranged for fluid communication between only said first stopcock and said pressure measurement chamber whereby said pressure measurement chamber is exposed to ambient atmospheric pressure for calibration.

10. The system of claim 6 wherein said first stopcock is arranged to block fluid communication from said second stopcock, said second stopcock is arranged for fluid communication between only said source of pressurized fluid and said pressure measurement chamber, and said third stopcock is arranged for fluid communication between only said pressure chamber and said ambient atmosphere whereby said pressure chamber is purged of air bubbles by said pressurized fluid.

11. The system of claim 6 wherein said control means comprises stepper motors connected to said stopcocks for selective step-wise adjustment thereof to provide desired fluid flow between certain ports and a programmable electrical signal-sending unit for sending electrical signals to said stepper motors appropriate to select desired fluid communications.

12. The system of claim 11 wherein said programmable electrical signal-sending unit is a central processing unit with user input means and drive circuitry to provide electric signals to selectively adjust said stepper motors, and appropriate software to automatically adjust said stepper motors responsive to user input and in the absence of user input.

13. The system of claim 11 wherein said programmable electrical signal-sending unit is a microprocessor with microchips with user input means and drive circuitry which provide electric signals to selectively adjust said stepper motors.

14. The system of claim 13 wherein said programmable electrical signal-sending unit is programmed to interrogate said user input means for user input to determine if one of the functions selected from pressure measurement, catheter flushing, calibration, and air purging has been selected, and
continues to operate in the vascular pressure measurement mode as a default condition in the absence of said user input and a flush inhibit input.

15. The system of claim 14 wherein said default condition pressure measurement mode further comprises flushing said system periodically.

16. The system of claim 14 wherein said flushing is maintained for a period of from about 1 to about 10 second every minute.

17. A method for continual external pressure measurement of fluid pressure in a human body in which automatic periodic flushing of fluid passages can be made and periodic calibration of pressure measurement devices can be made comprising:
providing at least two three-port stopcocks connected for fluid communication between a catheter tube leading to the body, the atmosphere, a source of pressurized flushing fluid, and a pressure measurement chamber of a pressure measurement device,
a first stopcock connected to said catheter and to a second stopcock for fluid communication therebetween in a first position, with a third port in communication with ambient atmosphere, for calibration with atmospheric pressure when said first stopcock is arranged for fluid communication between the atmosphere and said second stopcock,
a second stopcock connected to said first stopcock and said pressure measurement instrument for fluid communication therebetween in a first position with a third port in communication with said source of pressurized fluid for flushing said catheter of occlusions when said second stopcock is arranged for fluid communication between said source of pressurized fluid and said first stopcock, and for purging said pressure measurement device of bubble when second stopcock is arranged for fluid communication between said source of pressurized fluid and said pressure measurement device,
a port for purging said pressure measurement instrument which provides fluid communication for said pressurized fluid away from said pressure measurement instrument,
controlling said stopcocks by stepper motors mechanically linked for directly driving each said stopcock to a first position for fluid communication between said catheter and said pressure measurement device whereby vascular pressure measurement can be taken, to said catheter flush position, to said calibration position, and to said purging position, and
providing command means connected to said control means for delivery of command signals thereto whereby said selective fluid communication connections are effected.

18. The method of claim 17 wherein said control means includes a central processing unit with drive circuiting to provide electrical signal to selectively adjust said stepper motors, and one of software and micro-chips to automatically adjust said stepper motors responsive to user input and in the absence of user input.

19. Multi-function fluid communication control system for effecting selective automated simultaneous and step-wise connection for fluid communication between fluid reservoirs, fluid sources, instruments, and various pressure conditions, comprising
more than one stopcock multi-port fluid communication valve, each said stopcock having fluid path selection levers,
fluid passage conduits connecting ports of each of said stopcocks to provide said selective fluid communication between said fluid reservoirs, sources, instruments, and various pressure conditions responsive to command signals, said control means comprising stepper motors connected for selective step-wise adjustment of said stopcocks to provide desired fluid flow between certain ports and a programmable electrical signal-sending unit for sending electrical signals to said stepper motor, said stepper motors connected to said stopcocks by means of a linkage from an output drive armature of said motor to a means for directly driving said levers whereby said stopcocks are selectively adjusted, and command means connected to said control means for delivery of command signals thereto whereby said selective fluid communication connections are effected.

20. The method of claim 19 which further comprises programming said central processing unit to provide periodic flushing of said system.

21. The method of claim 20 wherein said flushing is maintained for a period of from about 1 to about 10 seconds every minute.

* * * * *